United States Patent [19]

Umezawa et al.

[11] Patent Number: 5,101,022
[45] Date of Patent: Mar. 31, 1992

[54] MYCAMINOSYL TYLONOLIDE DERIVATIVES

[75] Inventors: Hamao Umezawa; Sumio Umezawa, both of Tokyo; Tsutomu Tsuchiya, Kanagawa; Tomio Takeuchi, Tokyo; Akihiro Tanaka, Tokyo; Shuichi Sakamoto, Tokyo, all of Japan

[73] Assignee: Yamanouchi Pharmaceutical Co., Ltd., Tokyo, Japan

[21] Appl. No.: 650,060

[22] Filed: Feb. 4, 1991

Related U.S. Application Data

[60] Continuation of Ser. No. 511,839, Apr. 20, 1990, which is a continuation of Ser. No. 383,190, Jul. 20, 1989, abandoned, which is a division of Ser. No. 244,500, Sep. 14, 1988, Pat. No. 4,914,192, which is a division of Ser. No. 861,537, May 9, 1986, Pat. No. 4,794,173.

[30] Foreign Application Priority Data

May 13, 1985 [JP] Japan .................. 60-102402

[51] Int. Cl.$^5$ .................. C07H 17/08
[52] U.S. Cl. .................. 536/7.1
[58] Field of Search .................. 536/7.1; 514/30

[56] References Cited

U.S. PATENT DOCUMENTS

| | | | |
|---|---|---|---|
| 4,415,730 | 11/1983 | Fujiwara et al. | 536/7.1 |
| 4,421,911 | 12/1983 | Fujiwara et al. | 536/7.1 |
| 4,794,173 | 12/1988 | Umezama et al. | 536/7.1 |

FOREIGN PATENT DOCUMENTS 0042697  3/1982  Japan .................. 536/7.1

Primary Examiner—Johnnie R. Brown
Assistant Examiner—Elli Peseley
Attorney, Agent, or Firm—Burgess, Ryan & Wayne

[57] ABSTRACT

Mycaminosyl tylonolide derivatives represented by the following general formula

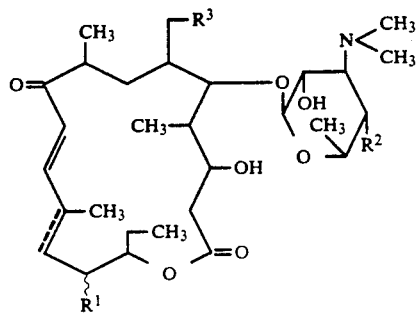

(wherein $R^1$ denotes hydroxyl group, a lower alkanoyloxy group, benzoyloxy group, azido group, or amino group which may optionally be substituted with a lower alkyl or a lower alkanoyl radical; $R^2$ stands for hydrogen atom or hydroxyl group; $R^3$ expresses hydrogen atom or formyl group; and ═ means a double bond or a radical represented by

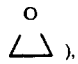

and salts thereof.

1 Claim, No Drawings

MYCAMINOSYL TYLONOLIDE DERIVATIVES

This is a continuation of application Ser. No. 511,839, filed Apr. 20, 1990 still pending, which is a continuation of U.S. 383,190, filed July 20, 1989, now abandoned which is a divl. appln. of U.S. Ser. No. 244,500, filed Sep. 14, 1988, now U.S. Pat. No. 4,904,192, which is a divl. appln. of U.S. Ser. No. 861,537, filed May 9, 1986, now U.S. Pat. No. 4,794,173.

BACKGROUND OF THE INVENTION

Various mycaminosyl tylonolide derivatives have been known so far. However, mycaminosyl tylonolide derivatives are not known wherein an unsubstituted or substituted amino group, etc. is directly attached to the 14-position of the derivatives.

The compounds of this invention are novel compounds having excellent antibacterial activity, and have a characteristic in that the 14-position has a substituent selected from a hydroxyl group, a lower alkanoyloxy group, benzoyloxy group, azide group, or amino group which may optionally be substituted with a lower alkyl group or a lower alkanoyl group.

The subject matter of this invention is directed to such particular novel compounds, and the production methods for the compounds. The compounds also include the salts thereof such as acid addition salts.

DETAILED EXPLANATION OF THE INVENTION

Technical Field

This invention relates to macro-lactone compounds having a broad spectrum of antibacterial activity against Gram-positive and -negative bacteria. More particularly it relates to new 14-substituted mycaminosyl tylonolide derivatives represented by the following general formula (I)

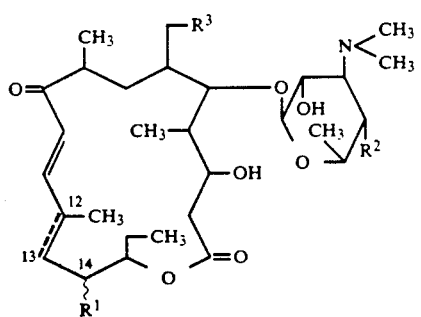

(wherein $R^1$ denotes hydroxyl group, a lower alkanoyloxy group, benzoyloxy group, azide group, or amino groups which may optionally be substituted with lower alkyl or a lower alkanoyl radical; $R^2$ stands for hydrogen atom or hydroxyl group; $R^3$ expresses hydrogen atom or formyl group; and ▬ means a double bond or a radical represented by

and salts thereof.

Description of the Prior Art

A large number of patents have been filed on mycaminosyl tylonolide derivatives. For example, U.S. Pat. No. 4,438,109 filed by the present inventors discloses a wide variety of compounds in which the 23-position carbon of the macro-lactone ring has substituent groups such as hydroxyl, alkanoyloxy radicals and arylcarbonyloxy radicals; and European Patent Application (Laid-open) No. 70,170 also filed by the present inventors discloses compounds in which substituent groups at the 23-position carbon in the macro-lactone ring are hydroxyl, halogen atoms and radicals represented by

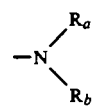

(wherein $R_a$ is hydrogen atom or a lower alkyl which may optionally be substituted with hydroxyl group, and $R_b$ is hydrogen atom, aryl, aralkyl or a lower alkyl, aryl or aralkyl which may optionally be substituted with hydroxyl group).

However, the compounds of this invention are distinctly different in structure from the compounds mentioned above; the compounds of this invention are new mycaminosyl tylonolide derivatives and salts thereof which have never been found in nature, are very difficult to synthesize, and are characterized in that hydroxyl group, a lower alkanoyloxy group, benzoyloxy group, azido group, or amino group which may optionally be substituted with lower alkyl or a lower alkanoyl radical, is directly attached to the 14-position.

In addition, the compounds of this invention have a broad spectrum of antibacterial activity against Gram-positive and -negative bacteria as detailed below.

Illustrative Examples of the Objective Compounds

The compounds defined by the general formula (I) shown above will be described below in more detail. "Lower alkyl groups" herein mean linear or branched alkyl groups of 1 to 6 carbon atoms, such as methyl, ethyl, n-propyl, ispropyl, n-butyl, isobutyl, tert-butyl and n-pentyl.

"Lower alkanoyl groups" herein means linear or branched alkanoyl groups of 1 to 6 carbon atoms, such as acetyl, propionyl, isopropionyl, butyryl, tert-butyryl and valeryl; and "lower alkanoyloxy groups" herein means radicals in which oxygen atom has been attached to the carbonyl of "lower alkanoyl groups", such as acetoxy, propionyloxy, isopropionyloxy, butyryloxy, t-butyryloxy, valeryloxy and hexanoyloxy.

"Amino groups which may optionally be substituted with a lower alkyl or lower alkanoyl group" include unsubstituted amino, methylamino, dimethylamino, ethylamino, ethylmethylamino, diethylamino, propylamino, isopropylamino, butylamino, butylmethylamino, acetamide, butyramide and pentanamide groups.

Each of the compounds of this invention (having an asymmetric carbon at 14-position of the macro-lactone ring) exists in two stereoisomeric forms depending on whether the substituent group $R^1$ at 14-position is attached in α- or β-conformation. It is needless to say that all these stereoisomers and mixtures thereof are includes in the scope of this invention.

The macro-lactone compounds of this invention form salts with various acids, etc. These acids include inorganic acids such as hydrochloric, hydrobromic, hydroiodic, sulfuric, nitric and phosphoric acids, and organic acids such as formic, acetic, oxalic, citric, succinic, maleic, malic, tartaric, methanesulfonic, toluenesulfonic acid and ethanesulfonic acids. The salts of these acids can be prepared by usual methods.

The compounds of this invention (I) have a broad antibacterial spectrum against Gram-positive and -negative bacteria. Those having dimethylamino groups at 14-position in α-conformation, in particular, exhibit powerful activity against Gram-negative bacteria.

The table give on next page lists minimum growth-inhibition concentrations of compounds (I) against various bacteria.

TABLE (Minimum Growth-Inhibition Concentrations, γ/ml)

| Strain | MT | 1 | 2 | 3 | 5 | 6 | 7 |
|---|---|---|---|---|---|---|---|
| B. Subtilis NRRL B-558 | 3.12 | 3.12 | <0.2 | 0.39 | <0.2 | 0.78 | 0.78 |
| M. luteus PCI 1001 | <0.2 | <0.2 | <0.2 | <0.2 | <0.2 | 0.2 | <0.2 |
| Staph. aureus Smith | 1.56 | 0.78 | 0.39 | 0.39 | 0.78 | 0.78 | 0.39 |
| E. coli K-12 | 25 | 12.5 | 12.5 | 12.5 | 12.5 | 6.25 | 3.12 |
| Kl. pneumoniae PCI-602 | 3.12 | 1.56 | 12.5 | 12.5 | 3.12 | 3.12 | 1.56 |
| Sal. entiritidis 1891 | 3.12 | 1.56 | 3.12 | 3.12 | 3.12 | 0.78 | 1.56 |

MT: Micaminosyl Tylonolide

Process for Producing Objective Compounds

The objective compounds of this invention (I) can be prepared by any of the methods described below.

PROCESS 1

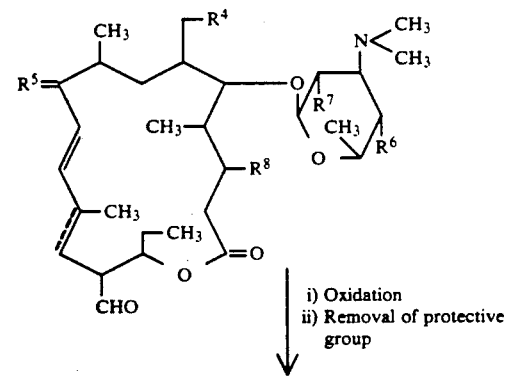

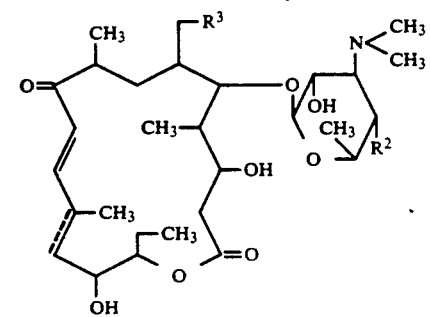

(wherein $R^4$ is hydrogen atom or formyl group which may optionally be protected, $R^5$ is oxygen atom or a protective groups for carbonyl; $R^6$ is hydrogen atom or hydroxyl which may optionally be protected; $R^7$ and $R^8$ are each hydroxyl which may optionally be protected; and $R^2$, $R^3$ and ⚌, are as defined above). Preferable protective groups are as follows:

Protective groups for formyl at $R^4$ and for carbonyl at $R^5$: Acetals, thioacetals, ketals and thioketals, such as dimethylacetal, diethylacetal, diethylthicacetal, ethyleneacetal, ethylenethioacetal, propyleneacetal, dimethylketal, diethylketal, diethylthioketal, ethyleneketal, ethylenethioketal and propyleneketal.

Protective groups for hydroxyls at $R^6$ and $R^7$; Lower acyls, such as acetyl, propionyl, butyryl, valeryl and isovaleryl.

Protective groups for hydroxyl at $R^8$: tert-Butyldimethylsilys, 2-tetrahydropyranyl and 2-tetrahydro furanyl.

This process involves two steps: (i) oxidation of the formyl group at 14-position of starting material (II) to form 14-formoxy-3'-dimethylaminooxide compound, and then (ii) reducing the formed compound in order to convert 14-formoxy to 14-hydroxy and to change 3'-dimethylamino-oxide to 3'-dimethylamino, and then, if any protective group is present, removing protective group(s).

i) The oxidation of the starting material (II) can be carried out in a conventional manner. That is, it can be carried out preferably by using a oxidation agent such as peroxy acid (for example, metal-chloro perbenzoic acid, peracetic acid, etc). It is preferable to add an organic alkaline salt (for example, sodium hydrogen carbonate, potassium hydrogen carbonate, sodium acetate, etc.) for the purpose of inhibiting side reactions. The oxidation can be carried out preferably in organic solvent such as chloroform, dichlorometane, etc.

(ii) Removal of the protective groups for the hydroxyls at $R^5$ and $R^7$ may be easily effective by heating in methanol, an aqueous alcohol or an aqueous aprotic solvent. The protective groups for the formyl at $R^4$, for the carbonyl at $R^5$ and for the carbonyl at $R^5$ can be removed by treatment with a mineral acid, such as hydrochloric and sulfuric acids, or an organic acid, such as acetic, trifluoroacetic and trichloroacetic acids. The protective groups for the hydroxyl at $R^8$ can be removed by treatment with tetra-butylammonium fluoride or potassium fluoride, etc., namely in neutral condition, or can be removed together with the protective groups for formyl at $R^4$ and the carbonyl at $R^5$ by treatment with a mineral acid (such as hydrochloric acid and sulfuric acid) or organic acid (such as acetic, trifluoroacetic and trichloroacetic acids).

PROCESS 2

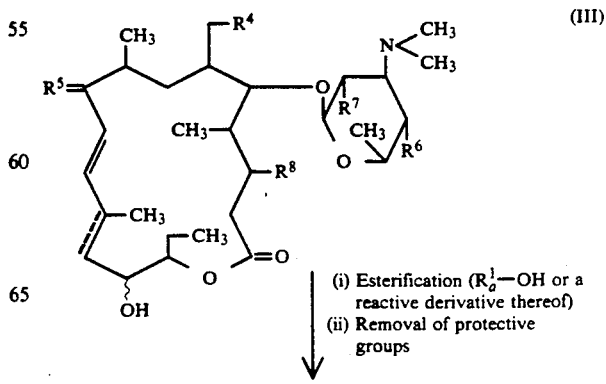

-continued

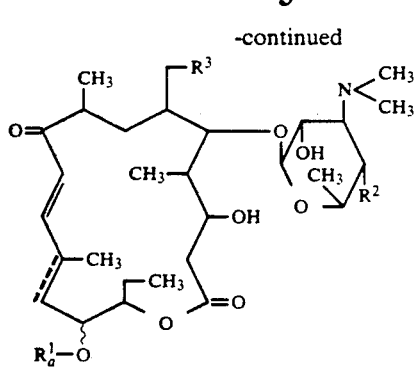

(wherein $R^1$ is a lower alkanoyl or benzoyl group; $R^4$ is hydrogen atom or formyl which may optionally be protected; $R^2$, $R^3$, ---, $R^5$, $R^6$, $R^7$ and $R^8$ are as defined above.

This process involves two steps: (i) esterification of the hydroxyl group at 14-position of starting material (III), and (ii) removal of protective groups if any.

Step (i)

Esterification of starting materials (III) may be effected by any known technique, preferably, by reactive with an acid anhydride (e.g., acetic anhydride, valeric anhydride and butyric anhydride) or an acid halide (e.g., acetyl chloride) in an organic solvent such as pyridine and diethylamine, etc. The DCC process (reaction of free carboxylic acids in pyridine or pyridinedimethylaminopyridine in the presence of dicyclohexylcarbodiimide) may also be adopted.

The esterification may also be effected by reacting formic acid, acetic acid, propionic acid, valeric acid, etc. (that is, free carboxylic acid it self) in the presence of diethyl azodicarboxylic acid, triphenylphosphine, etc. in a solvent such as dry toluene, dry oxolane, etc. In this case, the 14-conformation at 14-position in the case of the formed compound is reverse to that in the case of the starting material.

Step (ii)

Removal of protective group(s) may be effected in the manner similar to that at ii) in the before-mentioned Process 1.

PROCESS 3

Compound (III)
Azide formation

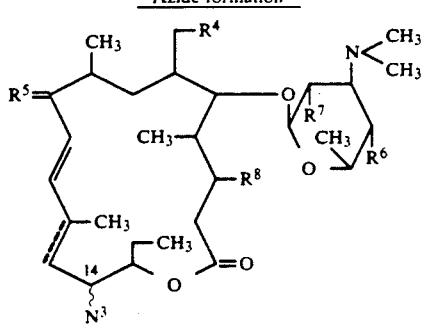

(b) Removal of protective groups   (a) (i) Amination
                                       (ii) Removal of protective groups -continued
Compound (III)
Azide formation

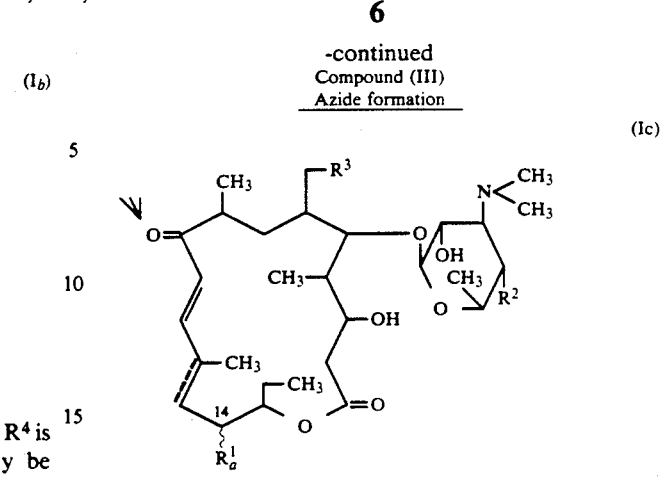

(wherein $R^1$ is azide or amino group which may optionally be substituted with a lower alkyl or lower alkanoyl radical; and $R^2$, $R^3$, ---, $R^4$, $R^5$, $R^6$, $R^7$ and $R^8$ are as defined above).

This process also involves two reaction steps: (1) aside formation at 14-position, and (2) amination, followed by removal of protective groups if any, or (b) direct removal of protective groups from the azide compounds.

Azide formation in step (1) is preferably carried out by reaction with axidodiphenylphosphoryl (or hydrazoic acid) in a solvent, such as anhydrous toluene and oxolane, in the presence of diethyl azodicarboxylate and triphenylphosphine.

Amination in step (2) can be easily effected by treatment of an azide compound (IV) with triphenylphosphine and water in a solvent such as oxolane and acetonitrile. It is possible, when desired, to introduce a lower alkyl or lower alkanoyl group to the amino compound thus obtained.

Introduction of a lower alkyl group, for example, may be achieved by reaction with an aldehyde (e.g., paraformaldehyde, acetaldehyde and propionaldehyde) in anhydrous methanol at room temperature or at an elevated temperature, followed by reduction with sodium cyanoborohydride, sodium borohydride or the like.

Lower alkanoyl groups can be introduced by reaction with an acid halide or acid anhydride (e.g., methyl chloroformate, ethyl chloroformate, acetyl chloride, propionyl chloride and acetic anhydride).

Removal of the protective groups can be effected in the same manner as in Process I.

PROCESS 4

Compound (III)

(Step 1) ↓ Introduction of leaving group

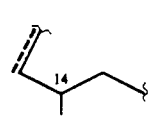

(Step 2) ↓ (i) Substitution reaction
           (ii) Removal of protective groups

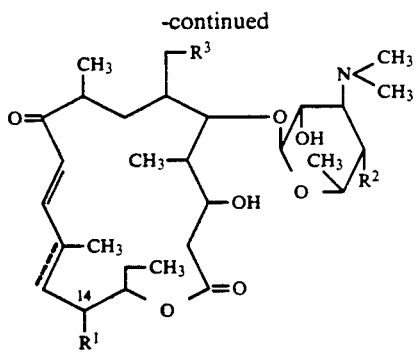

(wherein L is a leaving group; and $R^1$, $R^2$, $R^3$, and ⚌ are defined above).

This process consists of two steps: introduction a suitable leaving group to the C-14 hydroxyl in starting material (III) (Step 1), and subsequent substitution reaction (Step 2).

Preferable leaving groups to be introduced in Step 1 are organic sulfonic acid residues, such as tosyl and mesyl groups. These groups may be easily introduced by reaction of corresponding halides (e.g., tosyl chloride and mesyl chloride) in a solvent such as pyridine and triethylamide.

The reaction conditions of Step 2 are properly selected depending on the type of substituting group; for example, sodium azide, sodium acetate, alkylamines and sodium alcoholates are generally subjected to reaction in a solvent such as dimethylformamide and acetonitrile. Removal of the protective groups may be effected in the same manner as in Process 1.

OTHER PROCESSES

(A) Deformylation at 19-position

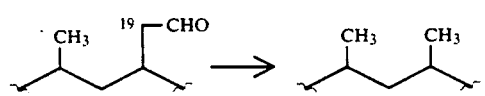

This process involves removal of formyl group at 19-position in mycaminosyl tylonolide derivatives. The reaction is preferably carried out by the action of chlorotris(triphenylphosphine)rhodium in an organic solvent, such as benzene and toluene, at room temperature or at an elevated temperature.

(B) Epoxidation at 12,13-double bond

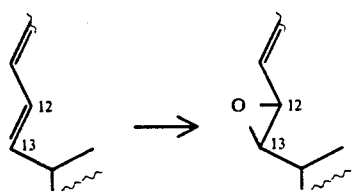

This process involves epoxidation at 12,13-double bond in mycaminosyl tylonolide derivatives. The reaction is preferably carried out by the action of m-chloroperbenzoic acid under cooling or under heating, followed by treatment with an acid.

(C) Dehydroxylation at 4'-position

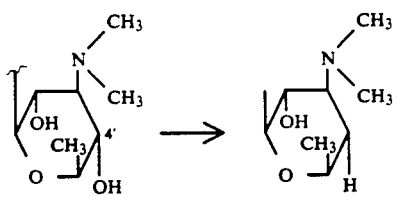

This process involves conversion of the hydroxyl at 4'-position in mycaminosyl tylonolide derivatives into hydrogen. The reaction is preferably carried out by the action of benzylsulfonium chloride in a solvent, such as pyridine, at a temperature of $-40°$ to $-30°$ C., followed by treatment with sodium iodide and tributyltin hydride in that order.

These reactions, (A), (B) and (C), may be adopted, as required, before, during or after any of Processes 1 through 4 described above.

As stated earlier, each of the compounds of this invention exists in two stereoisomeric forms ($\alpha$- and $\beta$-isomers at 14-C). In these isomers, the steric configuration can be inverted by the action of an organic acid (e.g., formic and acetic acids), hydrazoic acid or azidodiphenylphosphoryl, etc.—the method of Mitsunobu (Oyo Mitsunobu: Synthesis, 1981, 1–28). Hence, the esterification in Process 2 in the case of using diethyl azodicarboxylyl and triphenylphosphine as well as the azide formation reaction in Process 3 by using azidodiphenylphosphoryl, which is no other than the reaction of the above Mitsunobu method, is accompanied by inversion of steric configuration at 14-position ($\alpha$- to $\beta$-conformation, or vice versa).

It is also known that the substituent reaction in Process 4 is generically accompanied by inversion of steric configuration.

One may thus understand that, in the process of this invention, a desired compound having a desired steric configuration at 14-position can be obtained by using a starting material having 14-hydroxyl group of a specific configuration.

The reaction products obtained by the processes described above are treated by extraction with organic solvents, recrystallization, filtrations, reprecipitation, column chromatography and other known techniques, giving pure products.

The pure compounds (I) thus obtained may be formed into tablets, powder, granules, capsules, injectable liquids and other pharmaceutical preparations for oral and parenteral administration. Suitable daily dose is 10 mg to 100 mg (given once to four times a day); that is, a daily total of 10 to 1,000 mg is usually administered in one to four doses.

The following Examples further detail the preparative methods of the compounds of this invention. Some of the starting materials used for the synthesis thereof are novel compounds, so their manufacturing methods are also shown in the following Reference Examples.

COMPOUNDS OF EXAMPLES

[Structure of the compound with R¹, R², R³ substituents shown]

| Ex. No. | R¹ | R² | R³ | ----- |
|---|---|---|---|---|
| 2 | β-CH₃COO— | OH | CHO | = |
| 3 | β-(CH₃)₂CHCH₂COO— | " | " | " |
| 4 | β-CH₃CH₂COO— | " | " | " |
| 5 | β—⟨C₆H₄⟩—COO— | " | " | " |
| 6 | α-(CH₃)₂N— | " | " | " |
| 7 | α-(CH₃)₂N— | H | " | " |
| 8 | α-CH₃COO— | OH | " | " |
| 9 | α-CH₃CH₂COO— | " | " | " |
| 10 | β-(CH₃)₂N— | " | " | " |
| 12 | α-CH₃CO—NH— | " | " | " |
| 13 | α-(CH₃)₂N— | H | H | " |
| 14 | α-(CH₃)₂N— | " | CHO | epoxide |
| 1 | β-OH | OH | CHO | = |
| 11 | α-OH | " | " | " |

REFERENCE EXAMPLE 1

Hycaminosyl tylonolide diethylacetal (38.5 g) was dissolved in a mixture of 800 ml benzene and 200 ml sulfolane, ethylene glycol (37 ml), pyridine p-toluenesulfonate (18 g) and p-toluenesulfonic acid (5.5 g) were added, and the resulting mixture was heated under reflux for 48 hours according to the method of Tsuchiya [Jpn. J. Antibiotics, 32(Suppl.) (1979), S129-135]. The reaction mixture was poured into an aqueous saturated solution of sodium bicarbonate, and the mixture was extracted separately with benzene and chloroform. Each organic layer was treated as usual, the solvent was distilled off, and the residue was purified by silica gel column chromatography (chloroform/methanol/28%-ammonia: 30/1/0.1~18/1/0.1), giving pure mycaminosyl tylonolide 9,20-diethyleneacetal (yield: a total of 24.4 g). It showed the following properties:

$[\alpha]_D^{20} + 12°$ (c1, CHCl₃)

| NMR spectrum (CDCl₃): | | |
|---|---|---|
| δ (ppm) | Number of H | Assignment |
| 1.76 | 3H | Me-22 |
| 2.50 | 6H | NMe₂ |
| 5.75 | 1H | H-10 |
| 6.36 | 1H | H-11 |

REFERENCE EXAMPLE 2

Acetic anhydride (5.6 g) was added to a solution of mycaminosyl tylonolide 9,20-diethyleneacetal (17.2 g) in 172 ml acetonitrile, and the mixture was continuously stirred overnight. After concentrating the reaction mixture, the residue was extracted with benzene, and the extract was worked up as usual, affording 17.4 g of 2',4'-di-O-acetylmycaminosyl tylonolide 9,20-diethyleneacetal as solid. It showed the following properties:

$[\alpha]_D^{22} - 17°$ (c1, CHCl₃)

| NMR spectrum (CDCl₃): | | |
|---|---|---|
| δ (ppm) | Number of H | Assignment |
| 1.75 | 3H | Me-22 |
| 2.01 | 3H | Ac |
| 2.05 | 3H | Ac |
| 2.34 | 6H | NMe₂ |
| 4.65 | 1H | H-1' |

REFERENCE EXAMPLE 3

Tert-butylchlorodimethylsilane (17 g) was added to a solution of 17.4 g 2',4'-di-O-acetylmycaminosyl tylonolide 9,20-diethyleneacetal and 9.2 g imidazole in 140 ml N,N-dimethylformamide, and the mixture was heated at 80° C. for nine hours. After concentrating the reaction mixture, the residue was extracted with benzene, and the extract was worked up as usual, affording 22 g of 2',4'-di-O-acetyl-3,23-di-O-tert-butyldimethylsilylmycaminosyl tylonolide 9,20-diethyleneacetal as solid. It showed the following properties:

$[\alpha]_D^{22} - 58°$ (c1, CHCl₃)

| NMR spectrum (CDCl₃): | | |
|---|---|---|
| δ (ppm) | Number of H | Assignment |
| 1.71 | 3H | Me-22 |
| 2.05, 2.06 | 3H | Ac × 2 |
| 2.35 | 6H | NMe₂ |
| 4.45 | 1H | H-1' |

REFERENCE EXAMPLE 4

1M solution of tetrabutylammonium fluoride in oxolane (20 ml) was added to a solution of 22 g 2',4'-di-O-acetyl-3,23-di-O-tert-butyldimethylsilylmycaminosyl tylonolide 9,20-diethyleneacetal in 220 ml oxolane, and the mixture was allowed to stand at room temperature for two hours. After concentrating the reaction mixture, the residue was extracted with benzene, the extract was worked up as usual, the solvent was distilled off, and the residue was purified by silica gel column chromatography (toluene/ethyl acetate: 1/1~½), giving 16 g of pure 2',4'-di-acetyl-3-O-tert-butyldimethylsilyl-mycaminosyl tylonolide 9,20-diethyleneacetal as solid. It showed the following properties:

$[\alpha]_D^{20} - 54°$ (c1, CHCl$_3$)

| NMR spectrum (CDCl$_3$): | | |
|---|---|---|
| δ (ppm) | Number of H | Assignment |
| 0.89 | 9H | Si—tBu |
| 1.75 | 3H | Me-22 |
| 2.05, 2.06 | 3H | Ac × 2 |
| 2.34 | 6H | NMe$_2$ |
| 4.44 | 1H | H-1' |

REFERENCE EXAMPLE 5

2',4'-di-O-acetyl-3-O-tert-butyldimethylsilyl-mycaminosyl tylcnolide 9,20-diethyleneacetal (5.02 g) was dissolved in a mixture of 25 ml benzene and 25 ml dimethylsulfoxide, 1.67 g of pyridinium trifluoroacetate and 2.37 g of N,N'-dicyclohexylcarbodiimide were added in that order, and the resulting mixture was continuously stirred at room temperature overnight. The reaction mixture was poured into a solution of 0.97 g oxalic acid dihydrate in 20 ml dioxane, the precipitate was filtered off, and the filtrate was concentrated. The residue was dissolved in benzene, the solution was worked up as usual, and the solvent was distilled off, affording 4.7 g of 2',4'-di-O-acetyl-3-O-tertbutyldimethylsilyl-23-deoxy-23-oxomycaminosyl tylonolide 9,20-diethyleneacetal as solid. It showed the following properties:

| NMR spectrum (CDCl$_3$): | | |
|---|---|---|
| δ (ppm) | Number of H | Assignment |
| 1.80 | 3H | Me-22 |
| 2.07 | 6H | Ac × 2 |
| 2.38 | 6H | NMe$_2$ |
| 9.67 | 1H | H-23 |

REFERENCE EXAMPLE 6

Sodium bicarbonate (1.4 g) was added to a solution of 4.7 g 2',4'-di-O-acetyl-3-O-tert-butyldimethylsilyl-23-deoxy-23-oxomycaminosyl tylonolide 9,20-diethyleneacetal in 90 ml chloroform, 3.01 g of m-chloroperbenzoic acid was further added at room temperature, and the mixture was stirred for three hours. The reaction mixture was extracted with chloroform, the organic layer was worked up as usual, and the solvent was distilled off. The residue was then dissolved in toluene, 4.2 ml triphenyl phosphite was added to the solution, and the mixture was kept stirred overnight at room temperature. The reaction mixture was subjected to silica gel column chromatography (toluene/ethyl acetate: 3/1), giving 1.22 g of 2',4'-di-O-acetyl-3-O-tert-butyldimethylsilyl-14-dehydroxymethyl-14-β-formoxymycaminosyl tylonolide 9,20-diethyleneacetal as solid. It showed the following properties:

$[\alpha]_D^{20} - 35°$ (c2, CHCl$_3$)

| NMR spectrum (CDCl$_3$): | | |
|---|---|---|
| δ (ppm) | Number of H | Assignment |
| 2.34 | 6H | NMe$_2$ |

| -continued | | |
|---|---|---|
| NMR spectrum (CDCl$_3$): | | |
| δ (ppm) | Number of H | Assignment |
| 5.49 | 1H | H-14 |
| 8.03 | 1H | OCHO |

REFERENCE EXAMPLE 7

A solution of 1.2 g 2',4'-di-O-acetyl-3-O-tert-butyldimethylsilyl-14-dehydroxymethyl-14-β-formoxymycaminosyl tylonolide 9,20diethyleneacetal in 24 ml methanol was heated at 50° C. overnight with stirring. After concentrating the reaction mixture, the residue was purified by silica gel column chromatography (chloroform/methanol/20%-ammonia: 30/1/0.1~10/1/0.1), affording 1.06 g of 3-O-tert-butyldimethylsilyl-14-dehydroxymethyl-14-β-hydroxymycaminosyl tylonolide as solid. It showed the following properties:

| NMR spectrum (CDCl$_3$): | | |
|---|---|---|
| δ (ppm) | Number of H | Assignment |
| 1.78 | 3H | Me-22 |
| 2.52 | 6H | NMe$_2$ |
| 5.51 | 1H | H-13 |
| 5.73 | 1H | H-10 |
| 6.35 | 1H | H-11 |

REFERENCE EXAMPLE 8

Acetic anhydride (0.3 ml) was added to a solution of 1.06 g 3-O-tert-butyldimethylsilyl-14-dehydroxymethyl-14-β-hydroxymycaminosyl tylonolide 9,20-diethyleneacetal in 11 ml acetonitrile, and the mixture was allowed to stand at room temperature overnight. After concentrating the reaction mixture, the residue was dissolved in chloroform, and the solution thus obtained was treated as usual, giving 1.04 g of 2',4'-di-O-acetyl-3-O-tert-butyldimethylsilyl-14-dehydroxymethyl-14-β-hydroxymycaminosyl tylonolide 9,20-diethyleneacetal as solid. It showed the following properties:

$[\alpha]_D^{20} - 61°$ (c2, CHCl$_3$)

| NMR spectrum (CDCl$_3$): | | | |
|---|---|---|---|
| δ (ppm) | Number of H | | Assignment |
| 0.90 | 9H | | Si—tBu |
| 1.73 | 3H | | Me-22 |
| 2.34 | 6H | | NMe$_2$ |
| 4.30 | 1H | $J_{13,14} = J_{14,15} = 10$ Hz | H-14 |
| 5.43 | 1H | | H-13 |
| 5.68 | 1H | | H-10 |
| 6.33 | 1H | | H-11 |

EXAMPLE 1

3-O-tert-butyldimethylsilyl-14-dehydroxymethyl-14-β-hydroxymycaminosyl tylonolide 9,20-diethyleneacetal (24 mg) was dissolved in 0.12 ml acetonitrile, 0.12 ml of 1N-HCl was added, and the mixture was allowed to stand at 37° C. overnight. An aqueous saturated solution of sodium bicarbonate was added to the reaction mixture to make it alkaline, the alkaline solution thus obtained was extracted with chloroform, and the extract was worked up as usual. After distilling off the solvent, the residue was purified by silica gel chromatography (chloroform/methanol/28%-ammonia:

15/1/0.1), affording 13 mg of 14-dehydroxymethyl-14-β-hydroxymycaminosyl tylonolide as solid. It showed the following properties:

$[\alpha]_D^{20} -24°$ (c1, CHCl₃)

| NMR spectrum (CDCl₃): | | |
|---|---|---|
| δ (ppm) | Number of H | Assignment |
| 1.83 | 3H | Me-22 |
| 2.50 | 6H | NMe₂ |
| 4.45 | 1H(t)  $J_{13,14} = J_{14,15} = 9$ Hz | H-14 |
| 5.83 | 1H(d) | H-13 |
| 6.34 | 1H | H-10 |
| 9.70 | 1H | H-20 |

EXAMPLE 2

2',4'-di-O-acetyl-3-O-tert-butyldimethylsilyl-14-dehydroxymethyl-14-β-hydroxymycaminosyl tylonolide 9,20-diethyleneacetal (40 mg), obtained in Reference Example 8, was dissolved in 0.2 ml pyridine, 11 μl acetic anhydride was added, and the mixture was allowed to stand at room temperature overnight. The reaction mixture was worked up as usual, the solvent was distilled off, the solid left was dissolved in 0.4 ml methanol, and the solution was heated at 50° C. overnight with stirring. After concentration to dryness, the residue was dissolved in a mixture of 0.2 ml acetonitrile and 0.2 ml 1N-HCl, and the solution was allowed to stand at 37° C. overnight. An aqueous saturated solution of sodium bicarbonate was added to the reaction mixture to make it alkaline, the alkaline solution thus obtained was extracted with chloroform, and the extract was worked up as usual. After distilling off the solvent, the residue was purified by silica gel column chromatography (chloroform/methanol/29%-ammonia: 30/1/0.1 ~ 15/1/0.1), affording 10.9 mg of 14-β-acetoxy-14-dehydroxymethylmycaminosyl tylonolide as solid. It showed the following properties:

$[\alpha]_D^{17} 0°$ (c1, CHCl₃)

| NMR spectrum (CDCl₃): | | |
|---|---|---|
| δ (ppm) | Number of H | Assignment |
| 1.92 | 3H | Me-22 |
| 2.11 | 3H | Ac |
| 2.50 | 6H | NMe₂ |
| 6.35 | 1H | H-10 |
| 7.27 | 1H | H-11 |

EXAMPLE 3

14-Dehydroxymethyl-14-β-isovaleryloxymycaminosyl tylonolide was prepared in the same manner as in Example 2 except that 42 μl valeric anhydride was used in place of 11 μl acetic anhydride (yield: 12.8 mg). It showed the following properties:

$[\alpha]_D^{17} -5°$ (c1, CHCl₃)

| NMR spectrum (CDCl₃): | | |
|---|---|---|
| δ (ppm) | Number of H | Assignment |
| 1.92 | 3H | Me-22 |
| 2.50 | 6H | NMe₂ |
| 6.36 | 1H | H-10 |
| 7.26 | 1H | H-11 |

EXAMPLE 4

14-Dehydroxymethyl-14-β-propionyloxymycaminosyl tylonolide was prepared in the same manner as in Example 2 except that 8 μl propionyl chloride was used in place of 11 μl acetic anhydride (yield: 14.4 mg). It showed the following properties:

$[\alpha]_D^{17} +4°$ (c1, CHCl₃)

| NMR spectrum (CDCl₃): | | |
|---|---|---|
| δ (ppm) | Number of H | Assignment |
| 1.93 | 3H | Me-22 |
| 2.51 | 6H | NMe₂ |
| 6.36 | 1H | H-10 |
| 7.26 | 1H | H-11 |

EXAMPLE 5

14-Dehydroxymethyl-14-β-benzoyloxymycaminosyl tylonolide was prepared in the same manner as in Example 2 except that 11 μl benzoyl chloride was used in place of 11 μl acetic anhydride (yield: 16.9 mg). It showed the following properties:

$[\alpha]_D^{17} -50°$ (c1, CHCl₃)

| NMR spectrum (CDCl₃): | | |
|---|---|---|
| δ (ppm) | Number of H | Assignment |
| 2.00 | 3H | Me-22 |
| 2.52 | 6H | NMe₂ |
| 6.39 | 1H | H-10 |
| 7.29 | 1H | H-11 |

REFERENCE EXAMPLE 9

Triphenylphosphine (530 mg) was added to a solution of 796 mg 2',4'-di-O-acetyl-3-O-tert-butyldimethylsilyl-14-dehydroxymethyl-14-β-hydroxymycaminosyl tylonolide 9,20-diethyleneacetal, obtained in Reference Example 8, in 8 ml anhydrous toluene, and the mixture was stirred until clear. The solution was then cooled to −30° C., azidodiphenylphosphoryl (0.43 ml) and diethyl azodicarboxylate (0.31 ml) were added, and stirring was continued for one and a half hour while allowing the temperatures to rise to 0° C. Benzene was added to the reaction mixture, the organic solution was worked up as usual, the solvents were distilled off, the residue was purified by silica gel column chromatography (hexane/ethyl acetate: 3/1 ~ 2/1), and a fraction containing, as main component, 2',4'-di-O-acetyl-14-β-azido-3-O-tert-butyldimethylsilyl-14-dehydroxymethylmycaminosyltylonolide 9,20-diethyleneacetal, was collected. The desired compound isolated after concentration showed the following properties:

IR 2110 cm⁻¹

| NMR spectrum (CDCl₃): | | |
|---|---|---|
| (ppm) | Number of H | Assignment |
| 2.31 | 6H | NMe₂ |
| 5.55 | 1H | H-10 |
| 6.27 | 1H | H-11 |

REFERENCE EXAMPLE 10

Triphenylphosphine (0.7 g) was added to a solution of 700 mg 2',4'-di-O-acetyl-14-β-azide-3-O-tert-butyldimethylsilyl-14-dehydroxymethylmycaminosyl tylonolide 9,20-diethyleneacetal in 1 ml oxolane, and the mixture was heated at 40° C. overnight with stirring. Water (0.2 ml) was added, and the resulting mixture was further heated at 40° C. overnight with stirring. After concentration the reaction mixture, the residue was purified by silica gel column chromatography (toluene-/ethyl acetate: 1/1 ~ toluene/acetone: 2/1), affording 440 mg 2′,4′-di-O-acetyl-14-α-amino-3-O-tert-butyldimethylsilyl-14-dehydroxymethylmycaminosyl tylonolide 9,20-diethyleneacetal. It showed the following properties;

| NMR spectrum (CDCl$_3$): | | |
|---|---|---|
| (ppm) | Number of H | Assignment |
| 2.00 | 6H | Ac × 2 |
| 2.32 | 6H | NMe$_2$ |
| 5.40 | 1H | H-10 |

REFERENCE EXAMPLE 11

A solution of 440 mg 2′,4′-di-O-acetyl-14-α-amino-3-O-tert-butyldimethylsilyl-14-dehydroxymethylmycaminosyl tylonolide 9,20-diethyleneacetal in 4.4 ml methanol was heated at 50° C. overnight. After concentrating the reaction mixture, the residue was purified by silica gel column chromatography (chloroform/methanol/28%-ammonia: 40/1/0.1 ~ 20/1/0.1), affording 383 mg 14-α-amino-3-O-tert-butyldimethylsilyl-14-dehydroxymethylmycaminosyl tylonolide 9,20-diethyleneacetal. It showed the following properties:

$[\alpha]_D^{20} - 73°$ (c1, CHCl$_3$)

| NMR spectrum (CDCl$_3$): | | |
|---|---|---|
| δ (ppm) | Number of H | Assignment |
| 1.78 | 3H | Me-22 |
| 2.50 | 6H | NMe$_2$ |
| 5.39 | 1H | H-10 |
| 6.18 | 1H | H-11 |

REFERENCE EXAMPLE 12

14-α-Amino-3-O-tert-butyldimethylsilyl-14-dehydroxymethylmycaminosyl tylonolide 9,20-diethyleneacetal (41 mg) was dissolved in 0.82 ml anhydrous methanol, 16 mg paraformaldehyde was added, and the mixture was heated at 65° C. for one hour with stirring. To the clear solution thus obtained was added 16 mg sodium cyanoborohydride under ice cooling, and the mixture was stirred for 30 minutes. After concentrating the reaction mixture, the residue was extracted with chloroform, the extract was worked up as usual, the solvent was distilled off, and the residue was purified by silica gel column chromatography (chloroform/methanol/28%-ammonia: 30/1/0.1), affording 33 mg of 3-O-tert-butyldimethylsilyl-14-dehydroxymethyl-14-α-dimethylaminomycaminosyl tylonolide 9,20-diethyleneacetal. It showed the following properties:

| NMR spectrum (CDCl$_3$): | | |
|---|---|---|
| δ (ppm) | Number of H | Assignment |
| 1.78 | 3H | Me-22 |
| 2.37 | 6H | 14-NMe$_2$ |
| 2.50 | 6H | 3′-NMe$_2$ |
| 5.42 | 1H | H-10 |
| 6.28 | 1H | H-11 |

EXAMPLE 6

3-O-tert-butyldimethylsilyl-14-dehydroxymethyl-14-α-dimethylaminomycaminosyl tylonolide 9,20-diethyleneacetal (30 mg), obtained in Reference Example 12, was dissolved in a mixture of 0.15 ml acetonitrile and 0.15 ml 1N-HCl, and the solution was allowed to stand at 37° C. overnight. An aqueous saturated solution of sodium bicarbonate (1 ml) was added, the mixture was extracted with chloroform, the extract was worked up as usual, the solvent was distilled off, and the residue was purified by silica gel column chromatography (chloroform/methanol/28%-ammonia: 25/1/0.1 ~ 20/1/0.1), affording 20.5 mg of 14-dehydroxymethyl-14-α-dimethylaminomycaminosyl tylonolide. It showed the following properties:

$[\alpha]_D^{20} - 15°$ (c1, CHCl$_3$)

| NMR spectrum (CDCl$_3$): | | |
|---|---|---|
| δ (ppm) | Number of H | Assignment |
| 1.86 | 3H | Me-22 |
| 2.34 | 6H | 14-NMe$_2$ |
| 2.50 | 6H | 3′-Me$_2$ |
| 6.23 | 1H | H-10 |
| 7.12 | 1H | H-11 |
| 9.76 | 1H | H-20 |

REFERENCE EXAMPLE 13

3-O-tert-butyldimethylsilyl-14-dehydroxymethyl-14-α-dimethylaminomycaminosyl tylonolide 9,20-diethyleneacetal (100 mg), obtained in Reference Example 12, was dissolved in 1 ml anhydrous pyridine, 35 mg benzylsulfonyl chloride was added at a temperature of −38° to −35° C., and the mixture was stirred for two hours. After adding 0.1 ml water, the reaction mixture was concentrated, the residue was treated with 5 ml benzene, the organic layer was worked up as usual, and the solvent was distilled off. The residue left was dissolved in 1 ml anhydrous butanone, 93 mg sodium iodide was added, and the mixture was heated at 80° C. for 30 minutes with stirring. At the end of reaction, 4 ml benzene was added, the resulting mixture was worked up as usual, and the solvents were distilled off. Anhydrous benzene (1 ml) and tributyl tin hydride (180 mg) were added, and the mixture was heated at 80° C. for 30 minutes with stirring. After concentrating the reaction mixture, the residue was purified by silica gel column chromatography (chloroform/methanol/28%-ammonia: 50/1/0.1 ~ 30/1/0.1 ~ 10/1/0.1), affording 69 mg of 3-O-tert-butyldimethylsilyl-14-dehydroxymethyl-4′-deoxy-14-α-dimethylaminomycaminosyl tylonolide 9,20-diethyleneacetal (with 17 mg of the starting material being recovered). It showed the following properties:

| NMR spectrum (CDCl$_3$): | | |
|---|---|---|
| δ (ppm) | Number of H | Assignment |
| 1.78 | 3H | Me-22 |
| 2.31 | 6H | 3′-NMe$_2$ |
| 2.37 | 6H | 14-NMe$_2$ |
| 5.42 | 1H | H-10 |
| 6.27 | 1H | H-11 |

REFERENCE EXAMPLE 14

3-O-tert-butyldimethylsilyl-14-dehydroxymethyl-4'-deoxy-14-α-dimethylaminomycaminosyl tylonolide 9,20-diethyleneacetal (50 mg) was dissolved in 1 ml oxolane, 0.3 ml of 1M tetrabutylammonium fluoride solution in oxolane was added, and the mixture was heated at 40° C. for three hours with stirring. After concentrating the reaction mixture, the residue was dissolved in 4 ml benzene, the solution was worked up as usual, the solvent was distilled off, and the residue was purified by silica gel column chromatography (chloroform/methanol/28%-ammonia: 30/1/0.1~15/1/0.1), affording 37.5 mg of 14-dehydroxymethyl-4'-deoxy-14-α-dimethylaminomycaminosyl tylonolide 9,20-diethyleneacetal). It showed the following properties:

| | NMR spectrum (CDCl$_3$): | |
|---|---|---|
| δ (ppm) | Number of H | Assignment |
| 2.31 | 6H | 3'-NMe$_2$ |
| 2.37 | 6H | 14-NMe$_2$ |
| 5.41 | 1H | H-10 |
| 6.26 | 1H | H-11 |

EXAMPLE 7

14-Dehydroxymethyl-4'-deoxy-14-α-dimethylaminomycaminosyl tylonolide 9,20-diethyleneacetal (71 mg), obtained in Reference Example 14, was dissolved in a mixture of 0.2 ml acetonitrile and 4 ml 0.1N-HCl, and the solution was allowed to stand at room temperature for seven hours. An aqueous saturated solution of sodium bicarbonate (1 ml) was added, the resulting mixture was extracted with chloroform, the extract was worked up as usual, the solvent was distilled off, and the residue was purified by silica gel column chromatography (chloroform/methanol/28%-ammonia: 30/1/0.1~20/1/0.1), affording 50.2 mg of 14-dehydroxymethyl-4'-deoxy-14-α-dimethylaminomycaminosyl tylonolide. It showed the following properties:

| | NMR spectrum (CDCl$_3$): | |
|---|---|---|
| δ (ppm) | Number of H | Assignment |
| 1.84 | 3H | Me-22 |
| 2.28 | 6H | 3'-NMe$_2$ |
| 2.35 | 6H | 14-NMe$_2$ |
| 6.24 | 1H | H-10 |
| 7.13 | 1H | H-11 |
| 9.76 | 1H | H-20 |

EXAMPLE 8

2',4'-di-O-acetyl-3-O-tert-butyldimethylsilyl-14-dehydroxymethyl-14-β-hydroxymycaminosyl tylonolide 9,20-diethyleneacetal (100 mg), obtained in Reference Example 8, was dissolved in 1 ml anhydrous benzene, 70 mg triphenylphosphine and 41 μl diethyl azodicarboxylate was added in that order, 16 μl glacial acetic acid was then added under ice cooling, and the mixture was stirred at room temperature for 30 minutes. Benzene was added to the reaction mixture, the solution was worked up as usual, the solvent was distilled off, and the residue was purified by silica gel column chromatography (toluene/ethyl acetate: 4/1~3/1~2/1). A fraction containing, as main component, 14-α-acyloxy derivative was collected and concentrated, the residue was dissolved in 1 ml methanol, and the methanolic solution was allowed to stand at 37° C. overnight. After concentrating the reaction mixture, the residue was purified by silica gel column chromatography (chloroform/methanol/28%-ammonia: 30/1/0.1), and a fraction containing, as main component, 3-O-tert-butyldimethylsilyl-14-dehydroxymethyl-14-α-acetoxymycaminosyl tylonolide 9,20-diethyleneacetal was collected. After concentration, the residue was dissolved in oxolane, 1 ml of 1M tetrabutylammonium fluoride solution in oxolane was added, and the mixture was allowed to stand at room temperature for three hours. The reaction mixture was concentrated, the residue was extracted with chloroform, the extract was worked up as usual, the solvent was distilled off, and the residue was purified by silica gel column chromatography (chloroform/methanol/28%-ammonia: 35/1/0.1~25/1/0.1). The product thus obtained was hydrolyzed using a mixture of acetonitrile and 0.1N-HCl, and the reaction mixture was subjected to silica gel column chromatography (chloroform/methanol/28%-ammonia: 30/1/0.1~22/1/0.1), affording 22.3 mg of 14-α-acetoxy-14-dehydroxymethylmycaminosyl tylonolide. It showed the following properties:

$[α]_D^{20} - 64°$ (c1, CHCl$_3$)

| | NMR spectrum (CDCl$_3$): | |
|---|---|---|
| δ (ppm) | Number of H | Assignment |
| 1.93 | 3H | Me-22 |
| 2.16 | 3H | Ac |
| 2.50 | 6H | NMe$_2$ |
| 6.34 | 1H | H-10 |
| 7.16 | 1H | H-11 |
| 9.71 | 1H | H-20 |

EXAMPLE 9

14-Dehydroxymethyl-14-α-propionloxymethylmycaminosyl tylonolide was prepared in the same manner as in Example 8, except that 19 μl propionic acid was used in place of acetic acid (yield: 19 mg). It showed the following properties:

$[α]_D^{20} - 57°$ (c1, CHCl$_3$)

| | NMR spectrum (CDCl$_3$): | |
|---|---|---|
| δ (ppm) | Number of H | Assignment |
| 1.95 | 3H | Me-22 |
| 2.50 | 6H | NMe$_2$ |
| 6.33 | 1H | H-10 |
| 7.16 | 1H | H-11 |
| 9.72 | 1H | H-20 |

REFERENCE EXAMPLE 15

2',4'-di-O-acetyl-3-O-tert-butyldimethylsilyl-14-dehydroxymethyl-14-β-hydroxymycaminosyl tylonolide 9,20-diethyleneacetal (436 mg), obtained in Reference Example 8, was dissolved in 4.4 ml anhydrous benzene, 300 mg triphenylphosphine and 0.17 ml diethyl azodicarboxylate were added in that order, 42 μl formic acid was then added under ice cooling, and the mixture was stirred at room temperature for 30 minutes. Benzene was added to the reaction mixture, the solution was worked up as usual, the solvent was distilled off, and the residue was subjected twice to silica gel column chromatography (toluene/ethyl acetate: 3/1). Fractions containing, as main component, 14-α-formoxy derivative were collected and concentrated, the residue was dissolved in 2.4 ml methanol, and the methanolic solution was heated at 60° C. overnight. After concentrating the reaction mixture, the residue was purified by silica gel column chromatography (chloroform/methanol/28%-ammonia: 30/1/0.1~20/1/0.1), and a fraction containing, as main component, the deacetylated product was collected. After concentration, the residue was dissolved in 2 ml anhydrous acetonitrile, 55 ml of acetic anhydride was added, and the mixture was allowed to stand at room temperature overnight. The reaction mixture was concentrated, the residue was dissolved in 25 ml chloroform, the solution was worked up as usual, the solvent was distilled off, and the residue was purified by silica gel column chromatography (toluene/ethyl acetate: 7/3~5/3), affording 189 mg of 2′,4′-di-O-acetyl-3-O-tert-butylmethylsilyl-14-dehydroxymethyl-14-α-hydroxymycaminosyl tylonolide 9,20-diethyleneacetal. It showed the following properties:

$[\alpha]_D^{20} - 63°$ (c1, CHCl$_3$)

| NMR spectrum (CDCl$_3$): | | |
|---|---|---|
| δ (ppm) | Number of H | Assignment |
| 1.76 | 3H | Me-22 |
| 2.04, 2.06 | 3H | Ac × 2 |
| 2.35 | 6H | NMe$_2$ |
| 5.42 | 1H | H-10 |
| 6.17 | 1H | H-11 |

REFERENCE EXAMPLE 16

2′,4′-di-O-acetyl-3-O-tert-butyldimethylsilyl-14-dehydroxymethyl-14-α-hydroxymycaminosyl tylonolide 9,20-diethyleneacetal (89.3 mg) was dissolved in 0.9 ml anhydrous oxolane, 59 mg triphenylphosphine, 49 μl azidodiphenylphosphoryl and 35 ml diethyl azodicarboxylate were added in that order at −30° C., and the temperature of the mixture was allowed to rise to 0° C. over a period of 1.5 hours. After concentrating the reaction mixture, the residue was extracted with 5 ml benzene, the extract was worked up as usual, the solvent was distilled off, and the residue was subjected to silica gel column chromatography (hexane/ethyl acetate: 3/1~2/1). Fractions containing 14-β-azide derivative were collected, and the combined solution was concentrated.

The solid thus obtained was dissolved in 0.7 ml oxolane, 40 mg triphenylphosphine was added, and the mixture was allowed to stand at 50° C. overnight. After adding 0.1 ml water, the resulting mixture was heated at 50° C. for ten hours with stirring. After concentrating the reaction mixture, the syrup left was dissolved in 1 ml methanol, and the solution was allowed to stand at 60° C. for six hours. The solvents were distilled off, and the residue was purified by silica gel column chromatography (chloroform/methanol/28%-ammonia: 30/1/0.1~20/1/0.1), affording 45 mg of 14-β-amino-3-O-tert-butyldimethylsilyl-14-dehydroxymethylmycaminosyl tylonolide 9,20-diethyleneacetal. It showed the following properties:

$[\alpha]_D^{20} - 64°$ (c1, CHCl$_3$)

| NMR spectrum (CDCl$_3$): | | |
|---|---|---|
| δ (ppm) | Number of H | Assignment |
| 1.74 | 3H | Me-22 |
| 2.50 | 6H | NMe$_2$ |
| 5.63 | 1H | H-10 |
| 6.30 | 1H | H-11 |

EXAMPLE 10

Paraformaldehyde (25 mg) was added to a solution of 50 mg 14-β-amino-3-O-tert-butyldimethylsilyl-14-dehydroxymethylmycaminosyl tylonolide 9,20-diethyleneacetal (obtained in Reference Example 16) in 0.5 ml anhydrous methanol, and the mixture was heated at 65° C. for 2.5 hours. Sodium cyanoborohydride (30 mg) was then added to the resulting clear solution under ice cooling, and stirring was continued for one hour. After concentrating the reaction mixture, the residue was extracted with chloroform, the extract was worked up as usual, and the solvent was distilled off. The solid left was dissolved in 0.5 ml oxolane, 0.13 ml of 1M tetrabutylammonium fluoride solution in oxolane was added, and the mixture was allowed to stand at room temperature for nine hours. The reaction mixture was again concentrated, the residue was extracted with chloroform, the extract was worked up as usual, the solvent was distilled off, and the residue was purified by silica gel column chromatography (chloroform/methanol/28%-ammonia: 30/1/0.1~20/1/0.1~15/1/0.1), affording 27 mg of 14-β-dimethylamino-debutylsilyl derivatives. It was dissolved in a mixt. of 0.14 ml acetonitrile and 1.1 ml of 0.1N-HCl, and the solution was allowed to stand at room temperature for six hours. An aqueous saturated solution of sodium bicarbonate was added, the mixture was extracted with chloroform, the extract was worked up as usual, the solvent was distilled off, and the residue was purified by silica gel column chromatography (chloroform/methanol/28%-ammonia: 30/1/0.1~10/1/0.1), giving 25 mg of 14-dehydroxymethyl-14-β-dimethylaminomycaminosyl tylonolide as solid. It showed the following properties:

$[\alpha]_D^{20} - 32°$ (c0.6, CHCl$_3$)

| NMR spectrum (CDCl$_3$): | | |
|---|---|---|
| δ (ppm) | Number of H | Assignment |
| 1.83 | 3H | Me-22 |
| 2.30 | 6H | 14-NMe$_2$ |
| 2.50 | 6H | 3′-NMe$_2$ |
| 6.29 | 1H | H-10 |
| 7.30 | 1H | H-11 |
| 9.71 | 1H | H-20 |

EXAMPLE 11

14-α-Acetoxy-14-dehydroxymethylmycaminosyl tylonolide (100 mg), obtained in Example 8, was dissolved in 2 ml of a 23%-ammonia: methanol mixture (1:10), and the solution was allowed to stand at 20° C. for five hours. After concentrating the reaction mixture, the residue was purified by silica gel column chromatography (chloroform/methanol/28%-ammonia: 20/1/0.1~10/1/0.1), giving 28 mg of 14-dehydroxymethyl-14-α-hydroxymycaminosyl tylonolide as solid. It showed the following properties:

| NMR spectrum (CDCl₃): | | |
|---|---|---|
| δ (ppm) | Number of H | Assignment |
| 1.98 | 3H | Me-22 |
| 2.52 | 6H | NMe₂ |
| 6.35 | 1H | H-10 |
| 7.18 | 1H | H-11 |
| 9.72 | 1H | H-20 |

EXAMPLE 12

14-α-Amino-3-O-tert-butyldimethylsilyl-14-dehydroxymethylmycaminosyl tylonolide 9,20-diethyleneacetal (30 mg), obtained in Reference Example 11, was dissolved in 0.6 ml of 60% aqueous methanol, and 9.6 mg sodium bicarbonate was added. To this mixture was added under ice cooling 5.9 μl methyl chloroformate, and stirring was continued for one hour. An aqueous saturated solution of sodium bicarbonate was then added, the mixture was extracted with chloroform, the extract was worked up as usual, the solvent was distilled off, and the residue was purified by silica gel column chromatography (chloroform/methanol/28%-ammonia: 30/1/0.1), giving 19.8 mg of 3-O-tert-butyldimethylsilyl-14-dehydroxymethyl-14-α-methylcarbamoylmycaminosyl tylonolide as solid. It was dissolved in a mixture of 0.1 ml acetonitrile and 0.1 ml 1N-HCl, and the mixture was allowed to stand at room temperature for five hours. An aqueous saturated solution of sodium bicarbonate was then added, the mixture was extracted with chloroform, the extract was worked up as usual, the solvent was distilled off, and the residue was purified by silica gel column chromatography (chloroform/methanol/28%-ammonia: 20/1/0.1~18/1/0.1), giving 11.5 mg of 14-dehydroxymethyl-14-α-methylcarbamoylmycaminosyl tylonolide as solid. It showed the following properties:

| NMR spectrum (CDCl₃): | | |
|---|---|---|
| δ (ppm) | Number of H | Assignment |
| 1.90 | 3H | Me-22 |
| 2.50 | 6H | NMe₂ |
| 3.71 | 3H | COOMe |
| 6.27 | 1H | H-10 |
| 7.10 | 1H | H-11 |
| 9.71 | 1H | H-20 |

EXAMPLE 13

14-Dehydroxymethyl-4'-deoxy-14-α-dimethylaminomycaminosyl tylonolide (50 mg), obtained in Example 7, was dissolved in 1 ml benzene, 95 mg chlorotris(triphenylphosphine)rhodium was added, and the mixture was heated at 80° C. for ten hours. The reaction mixture was filtered, washed with benzene, and the organic layers were combined. The combined solution was worked up as usual, the solvents were distilled off, and the residue was purified by silica gel column chromatography (chloroform/methanol/28%-ammonia: 30/1/0.1~20/1/0.1), giving 9.8 mg of 19-deformyl-14-dehydroxymethyl-4'-deoxy-14-α-dimethylaminomycaminosyl tylonolide as solid. It showed the following properties:

| NMR spectrum (CDCl₃): | | |
|---|---|---|
| δ (ppm) | Number of H | Assignment |
| 2.29 | 6H | 3'-NMe₂ |
| 2.36 | 6H | 14-NMe₂ |
| 6.26 | 1H | H-10 |

EXAMPLE 14

14-Dehydroxymethyl-4'-deoxy-14-α-dimethylaminomycaminosyl tylonolide 9,20-diethyleneacetal (45 mg), obtained in Reference Example 14, was dissolved in 0.45 ml chloroform, 40 mg m-chloroperbenzoic acid was added under ice cooling, and the mixture was allowed to stand at room temperature for one hour. The reaction mixture after adding chloroform, was worked up as usual, giving a solid product after distilling off the solvent. It was dissolved in 0.5 ml toluene, 0.05 ml triphenyl phosphite was added, and the mixture was continuously stirred overnight at room temperature. After concentration, 0.3 ml acetonitrile and 4 ml 0.1N-HCl were added, and the mixture was again allowed to stand at room temperatures overnight. After washing with benzene an aqueous saturated solution of sodium bicarbonate was then added, followed by extraction with chloroform. The extract was worked up as usual, the solvent was distilled off, and the residue was purified by silica gel column chromatography (chloroform/methanol/28%-ammonia: 30/1/0.1~15/1/0.1), giving 15 mg of 14-dehydroxymethyl-4'-deoxy-12,13-epoxy-14-α-dimethylaminomycaminosyl tylonolide as solid. It showed the following properties:

| NMR spectrum (CDCl₃): | | |
|---|---|---|
| δ (ppm) | Number of H | Assignment |
| 2.27 | 6H | 3'-NMe₂ |
| 9.72 | 1H | H-20 |

What is claimed is:

1. Mycaminosyl tylonolide derivative represented by the formula

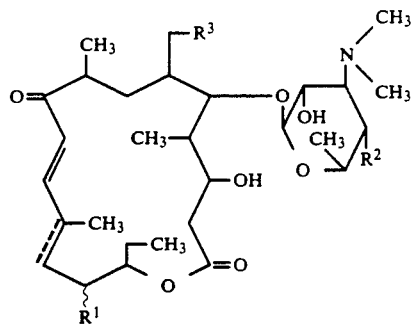

wherein $R^1$ represents a hydroxyl group; $R^2$ represents hydrogen or a hydroxyl group; $R^3$ represents hydrogen or a formyl group; and represents a double bond, or a pharmaceutically acceptable salt thereof.

* * * * *